(12) United States Patent
Dory et al.

(10) Patent No.: US 11,452,444 B2
(45) Date of Patent: Sep. 27, 2022

(54) MOVING IMAGE RENDERING USING EYE-TRACKING SENSOR SIGNAL

(71) Applicant: HEWLETT-PACKARD DEVELOPMENT COMPANY, L.P., Spring, TX (US)

(72) Inventors: Jon R. Dory, Fort Collins, CO (US); David H. Hanes, Fort Collins, CO (US); John Michael Main, Fort Collins, CO (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 368 days.

(21) Appl. No.: 16/495,305

(22) PCT Filed: Apr. 3, 2017

(86) PCT No.: PCT/US2017/025792
§ 371 (c)(1),
(2) Date: Sep. 18, 2019

(87) PCT Pub. No.: WO2018/186830
PCT Pub. Date: Oct. 11, 2018

(65) Prior Publication Data
US 2020/0093367 A1 Mar. 26, 2020

(51) Int. Cl.
*A61B 3/113* (2006.01)
*G06T 7/30* (2017.01)
*A61B 3/00* (2006.01)
*A61B 3/14* (2006.01)
*G06F 3/01* (2006.01)
*G06F 3/0484* (2022.01)

(52) U.S. Cl.
CPC ............ *A61B 3/113* (2013.01); *A61B 3/0041* (2013.01); *A61B 3/145* (2013.01); *G06F 3/013* (2013.01); *G06F 3/0484* (2013.01); *G06T 7/30* (2017.01)

(58) Field of Classification Search
CPC ....... A61B 3/113; A61B 3/0041; A61B 3/145; G06F 3/013; G06F 3/0484; G06T 7/30
USPC ....................................... 351/209
See application file for complete search history.

(56) References Cited

U.S. PATENT DOCUMENTS

| 8,594,381 B2 | 11/2013 | Fedorovskaya et al. |
| 2007/0273611 A1* | 11/2007 | Torch .................... A61B 3/112 345/8 |
| 2016/0167672 A1 | 6/2016 | Krueger |

(Continued)

FOREIGN PATENT DOCUMENTS

| WO | WO-2007085682 | 8/2007 |
| WO | WO-2016001902 | 1/2016 |

OTHER PUBLICATIONS

Smith, R.M. et al., Image-shifting Optics for a Nystagmus Treatment Device, Jun. 2004, < http://www.rehab.research.va.gov/jour/04/41/3a/oommen.html >.

*Primary Examiner* — Mohammed A Hasan
(74) *Attorney, Agent, or Firm* — Conley Rose PC

(57) ABSTRACT

A system is disclosed in which an eye-tracking sensor signal is received and a moving image is generated to be rendered on one or more displays based on the eye-tracking sensor signal. Responsive to an input control signal from a user-operable control device or based on a determination that the user's gaze direction is tracking the moving image, the system adjusts the moving image.

15 Claims, 5 Drawing Sheets

(56) References Cited

U.S. PATENT DOCUMENTS

2016/0262608 A1* 9/2016 Krueger ................ G06T 19/006
2016/0267716 A1* 9/2016 Patel ...................... G09G 5/373
2017/0024893 A1* 1/2017 Kruglick .............. G02B 27/017

* cited by examiner

MOVING IMAGE RENDERING USING EYE-TRACKING SENSOR SIGNAL

BACKGROUND

Nystagmus is a medical condition characterized by an involuntary, rapid, and repetitive movement of the eyes. Usually the movement is left-to-right (horizontal nystagmus), but it can also be up and down (vertical nystagmus). The condition usually involves both eyes.

People with nystagmus may tilt or turn their heads in an attempt to see more clearly. Children born with nystagmus may develop less clear vision. Acquired nystagmus may occur later in life for a variety of reasons. Adults who acquire nystagmus may see images as shaky.

BRIEF DESCRIPTION OF THE DRAWINGS

Various examples will be described below referring to the following figures.

DETAILED DESCRIPTION

In accordance with the various disclosed examples, a system is described to permit a person with a disorder such as nystagmus, in which the eyes move back and forth uncontrollably, to train neuropathways in the brain to slow down the speed of eye movement. In some examples, the system includes a virtual reality (VR) headset having one or more displays and eye-tracking sensors. The headset may be communicatively coupled to a console that produces images to be rendered on the headset's display and to receive sensor signals indicative of the direction of gaze of a user's eyes. Responsive to the sensor signals from the headset's eye-tracking sensors, the console generates an image on the display to track the movement of the user's eyes. As the movement of the image is generally synchronized to the movement of the user's eyes, the user may perceive the image to be stationary.

A user-operable control device can be used by the user to control the speed of the moving image. Once the console renders the moving image synchronized to the user's eye movements, the user can use the user-operable control device to cause the speed of the moving image to be adjusted. For example, the console may slow down the moving image in response to an input control signal from the user-operable control device. At that point, the moving image will still be moving on the display but at a slower speed than the user's eyes. Thus, the moving image will not be synchronized to the user's eye movements and the image may appear to the user to begin moving. The change in moving image speed may be relatively small and with time the user's brain may retrain itself to slow his or her eye movements to track the moving image. If and when that happens, the moving image will again appear to be stationary to the user. This process can be repeated with the console causing the moving image to be slowed down incrementally each time the user uses the user-operable control device to request the image speed to be adjusted.

Figure 1:
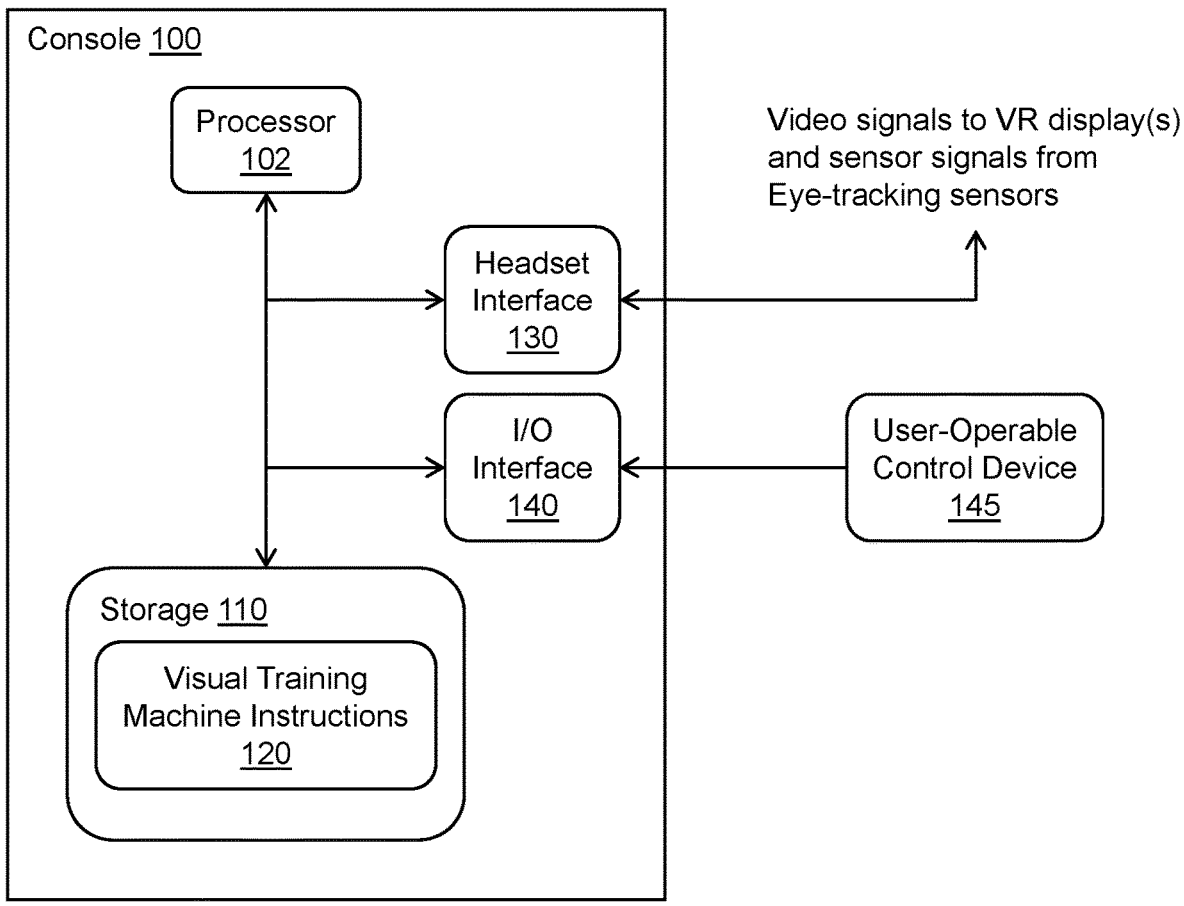
FIG. 1 shows an example of a system to retrain a user having nystagmus.

FIG. 1 shows an example system in which a console 100 includes processor 102, storage 110, a headset interface 130, and an input/output (I/O) interface 140. The storage 110 comprises a non-transitory storage device such as volatile memory (e.g., random access memory) or a non-volatile storage device (e.g., hard disk drive, solid state storage drive, etc.). The storage 110 includes visual training machine instructions 120, which comprise instructions that are executable by the processor 102. The processor 102 executes the visual training machine instructions 120 to perform some or all of the functionality described herein. While a single processor 102 is shown in the example of FIG. 1, other implementations include multiple processors. If more than one processor 102 is provided, some of the visual training machine instructions 120 may be executed by one processor while other of the instructions are executed by one or more other processors.

The headset interface 130 provides connectivity between the console 100 and a headset (e.g., a VR headset) worn by a user. The headset interface 130 may provide a wired or wireless communication link to the headset. The processor 102 (upon execution of the visual training machine instructions 120) may generate a video image for transmission to the display of the VR headset via the headset interface 130. The headset may include an eye-tracking sensor that determines the direction of gaze of one or both the user's eyes and provides an eye-tracking sensor signal to the console through the headset interface 130. The processor 102 then processes the eye-tracking sensor signals to determine the direction of gaze of the user and does so repeatedly to track the dynamically varying gaze direction of a person with nystagmus.

A user-operable control device 145 is coupled to the illustrative console 100 through the I/O interface 140. The user-operable control device 145 may include any type of user-activated input control such as a button, a knob, a joystick, a key on a keyboard, a hand or arm worn sensor, etc. The user-operable control device may be separate from, but coupled to (With a wire or wirelessly) the console 100, or it may be an integrated component of the console itself.

The headset may have a single display or multiple displays (one display for each eye). In one example, the headset comprises goggles with a built-in display (or multiple displays) with a strap that the user fits over their head. Examples of the display include an organic light emitting diode (OLED) display, a liquid crystal display (LCD), or other types of displays. In another example, the headset may have a slot or other type of receptacle into which a smart phone or other small form factor device with an electronic display can be installed. The display in this latter example is the display of the smart phone itself.

Figure 2:
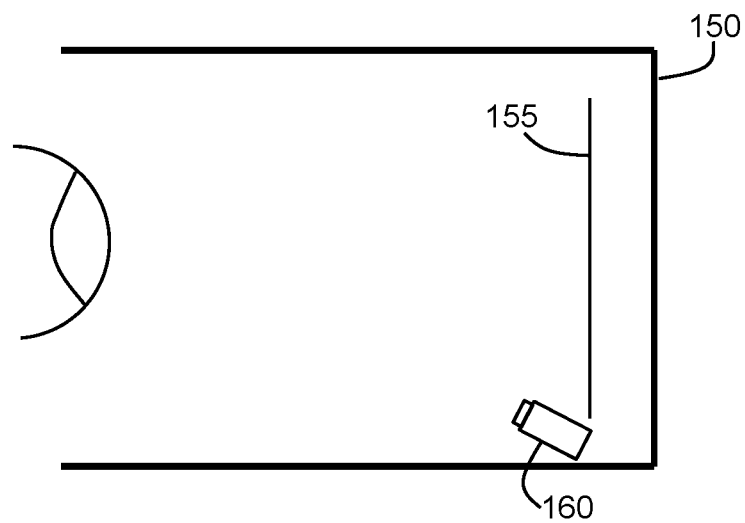
FIG. 2 illustrates a headset with a display and an eye-tracking sensor in accordance with various examples.

A single eye-tracking sensor may be included in the headset to track the movement of just one of the user's eyes, or multiple eye-tracking sensors may be provided, one sensor for each eye. FIG. 2 illustrates a portion of a side view of a headset 150. A user's eye is shown viewing a display 155 provided in the headset. An eye-tracking sensor 160 also is included to track the direction of gaze of the eye. One example of an eye-tracking sensor 160 includes a light source and a camera that captures light reflected off the user's eye. The light source may include an infrared (IR)

light source. The camera captures the reflected light which is then used to identify the reflection of the light source on the cornea and in the pupil. A vector formed by the angle between the cornea and the pupil reflections can be calculated and the direction of this vector, combined with other geometrical features of the reflection, can be used to calculate the gaze direction. The processor 102 may compute some or all of these computations.

To help train a person with nystagmus, the person puts on a headset and initiates (or a different person initiates) execution of the visual training machine instructions 120. The processor 102 executes the visual training machine instructions 120 to process the sensor signals from the eye-tracking sensor(s) of the headset 150 and to thereby determine the direction of gaze of the user's eye. In one example, separate eye-tracking sensors are provided, one for each eye, and thus the processor 102 can independently determine the gaze direction of each eye. In another example, a single eye-tracking sensor is included in the headset and the processor 102 determines a single gaze direction using that sensor's output signal.

In response to the determined gaze direction, the processor 102 generates an image to be rendered on the headset's display to track the gaze direction. As the eyes of a person with nystagmus move back and forth (horizontally or vertically), the direction of gaze dynamically and rapidly changes. The processor determines the dynamically changing gaze direction from the eye-tracking sensor and renders the image on the display to track the changing gaze direction.

Figure 3:
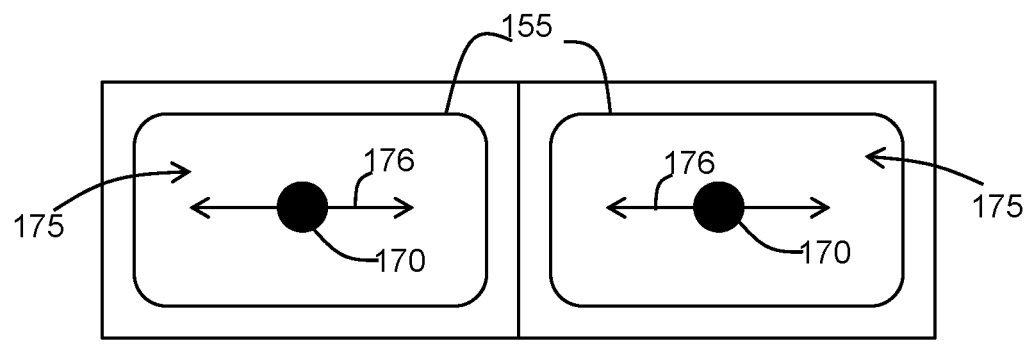
FIG. 3 illustrates the console rendering a moving image to track the movement of the user's eyes.

FIG. 3 shows an example of images rendered by the processor 102 comprising a geometric shape (e.g., a dot 170) on a solid background 175. FIG. 3 shows two displays 155, and a dot 170 is rendered on each display. The images rendered on the displays 155 can be other than a dot, and need not be a geometric shape. For a person with, for example horizontal nystagmus, the eyes move laterally left and right. The eye-tracking sensor signals are processed by the processor 102 to determine where each eye is pointing as they move back and forth and thus renders the images (e.g., the dot 170) to match the back and forth motion of the eyes. The dots 170 thus are rendered to move back and forth in sync with the user's eye movement as indicated by arrows 176.

After the training session begins, the processor 102 may take some time (e.g., a few seconds, a few minutes, etc.) to synchronize the moving image to the user's eye movements. Once the images are synchronized to the user's own eye movements, the dots will appear to be stationary to the user. Once the dots are stabilized for the user, the user can activate the user-operable control device 145.

The illustrative training system renders an image on a display to track the gaze direction of the user's eye(s). In one example, the image is rendered at the location on the display 155 at which the processor 102, based on the sensor signals from the eye-tracking sensors 160, determines the gaze direction to coincide. For example, if the processor determines that the user's eye is pointing at a certain location in the upper left-hand corner of the display, the image is rendered at that particular location. As the gaze direction changes, the processor 102 determines the locations across the display to which the user's eye is tracking and causes the image to be rendered at those locations as well. In such implementations, the display location at which the user's eye is pointing is the location at which the image is rendered.

In other implementations, the image is not rendered at the location at which the processor 102 determines the user's eye is pointing, but it still tracks the relative change in the gaze direction. For example, if the user's eye is moving laterally back and forth at a certain speed or oscillation frequency, the processor 102 renders the image on the display so as to also move back and forth laterally at the same speed and oscillation frequency and in phase with the user's eye movement. In one example, the headset may have one display and include an eye-tracking sensor that generates signals that permit the processor 102 to determine the movement of that eye. Assuming the user's eyes are generally aligned and are moving together back and forth in sync, the processor 102 may render the image on the display generally at the center point between the locations at which the person's eyes are pointing (or at another point on the display). While the rendered image may be offset from the location of gaze of the user's eyes, the image is rendered so as to approximately match the oscillation frequency and phase of the user's eye movement. If the user's eye is determined to be moving to the right at a certain speed, the image is rendered on the display also to move to the right at that same speed. In general, the processor 102 renders the image on the display to track the movement of the user's eyes, as determined from the eye-tracking sensor signals, and the image may or may not be rendered on the display directly in front of where either of the user's eyes is pointing.

The term "speed" as used herein may refer to the number of pixels (or other units of display resolution) of displacement per unit of time for the moving image. The term "oscillation frequency" (or simply "frequency") refers to the number of cycles that the user's eyes move per unit of time. The eyes of a person with nystagmus, however, may not oscillate back and forth with a single precise oscillation frequency. The period in which an eye moves in one direction and then back to the starting point may vary over time and even between consecutive oscillations. By rendering an image to track the relative movement of the user's eyes, the rendered image generally matches the speed and oscillation frequency of the user's own eye movements.

Figure 4:
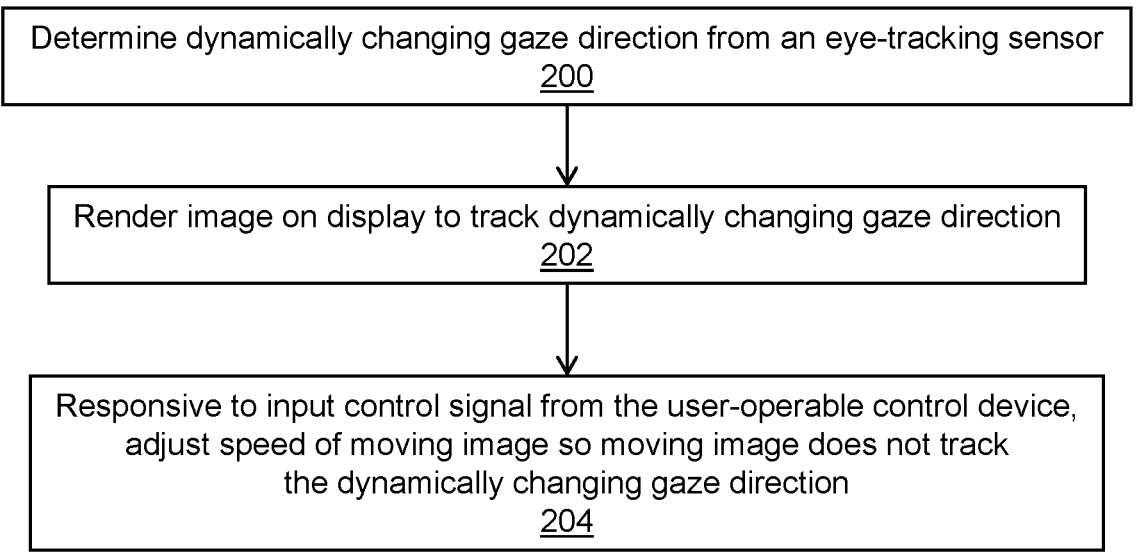
FIG. 4 shows a method in accordance with an example.

Referring to FIG. 4, an example method is shown for using the system described herein to help a person with nystagmus. The operations shown in FIG. 4 are described below with reference also to FIGS. 1 and 2. A user may put on the headset 150 and initiate execution of the visual training machine instructions such as through user activation of the console 100 (e.g., selecting the visual training machine instructions on a display (not shown) coupled to or integrated into the console 100).

At 200, the method includes determining the dynamically changing gaze direction from an eye-tracking sensor 160. This operation may be performed by the processor 102 receiving sensor signals from eye-tracking sensor(s) in the headset via the headset interface 130. The signals may be processed by the processor to determine a gaze direction for the user. The gaze direction may be represented as a location on the display at which the user's eye is determined to be pointing. Because the eyes of a person with nystagmus are continually moving, the gaze direction is repeatedly determined by the processor 102 based on the eye-tracking sensor signals. The processor may determine the gaze direction at a particular rate (e.g., 5 times per second).

At 202, the method includes rendering an image (e.g., a geometric shape such as a dot) on the headset's display(s) to track the dynamically changing gaze direction. As explained above, the rendered image tracking the changing gaze direction may include rendering the image on the display at the precise location at which the user's eye is pointing, or another location offset from the display location at which the eye is pointing but still moving at generally the same speed and direction as the eye movement and having the same general oscillation frequency.

Once the image is rendered on the display and tracks the user's own eye movements, the image should appear to be stationary to the user with nystagmus. At that point, the user can activate the user-operable control device 145 to signal the console to adjust the speed of the moving image. Thus, responsive to the input control signal from the user-operable control device, at 204, the method includes adjusting the speed of the moving image so that the rendered moving image no longer tracks the dynamically changing gaze direction.

The adjustment to the speed of the rendered moving image may be to decrease its speed or increase its speed. The user is ultimately trying to retrain the brain to make the eyes move less rapidly. To that end, the user may use the user-operable control device 145 to cause the image to slow down (e.g., decrease the oscillation frequency of the image). The processor 102 responds to the input control signal from the user-operable control device by rendering the image on the display 155 at a slower speed and thus lower oscillation frequency. The processor 102 may render the moving image to track the eye movements based on the eye-tracking sensor signals and then calculate the resulting oscillation frequency of the moving image. In one example, the image currently may be rendered so as to move laterally across the display in an oscillatory-like manner with an average horizontal oscillation frequency of 3 cycles per second. That is, the image completes a round trip across the display and back three times per second. To slow down the image, the processor may continue to render the image on the display in the same oscillatory-like manner but at a lower frequency such as 2.5 cycles per second.

The change in the speed of the moving image may be preconfigured in that the input control signal from the user-operable control device 145 indicates to the processor 102 that the speed is to be reduced, and the processor is programmed to lower the speed by a predetermined amount (e.g., expressed as a percentage). In this example, the user activating the user-operable control device 145 may not have any control over how much the speed of the moving image is adjusted each time a request is made to lower the image's speed. The user activates the user-operable control device, and the speed of the image automatically changes by a predefined amount.

In another example, the user activating the user-operable control device 145 has control over the amount that the speed is adjusted. In some implementations, the user-operable control device 145 comprises a rotatable knob, joystick, or other type of input control device that a user can use to indicate a speed change for the Moving image. In yet another example, a value can be entered on a keyboard indicative of how much the speed of the moving image should be adjusted (e.g., 5% slower). In such implementations, the input control signal from the user-operable control device 145 is indicative of the amount by which the speed and oscillation frequency of the moving image is to be changed.

Once the moving image is rendered at a lower speed, the moving image will no longer track the user's eye movements, and thus to a person with nystagmus the image will appear to move. However, by staring at the relatively slowly moving image (i.e., moving relatively slowly with respect to the user's eye movements), the user's neural pathways may be retrained to slow down his eye movements. When that happens, the image will again appear to be stationary. The user then can again activate the user-operable control device 145 to further adjust (e.g., slow down) the speed of the moving image.

If the user is unable to retrain the neuro-control of his eyes to make the slowly moving image become stationary (by slowing down his own eye movements), the user can activate the user-operable control device 145 to increase the speed of the moving image. For example, the user may want to slightly increase the speed of the moving image in an attempt to re-stabilize the image relative to his eye movements. The amount of speed and oscillation frequency increase may be preconfigured or manually selected by the user. Once the image is again stabilized, the user can activate the user-operable control device 145 to signal the console 100 to slow down the moving image in another attempt to slow down his eye movements. Thus, the user can increase or decrease the speed of the moving image during the training session.

In some examples, a second person (e.g., a healthcare professional) other than the user wearing the headset 150 activates the user-operable control device 145. The second person can decide when to change the speed of the moving image. The system may include an additional output interface to provide feedback to the non-headset wearing person as to the ability of the user's eyes to track the moving image. The information provided to the second person may be a value or alphanumeric message that indicates the degree to which the user's eyes are tracking the moving image. Once the second person determines that the user's eyes are sufficiently tracking the moving image, the second person may further adjust the speed of the image as described herein.

Figure 5:
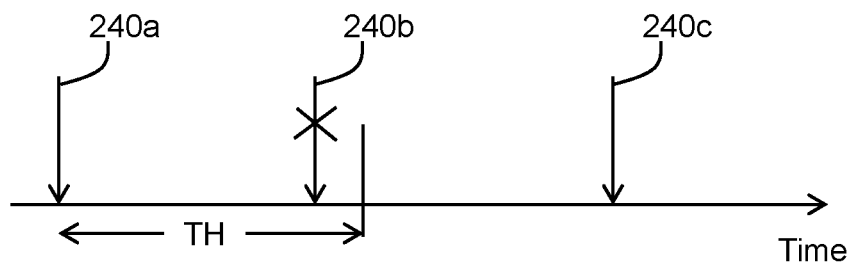
FIG. 5 illustrates an example of the implementation of a time period during which input control signals to adjust the speed of a moving image are ignored.

Some example systems may impose a time period following activation of the user-operable control device 145 to adjust the speed of the moving image during which further input control signals from the user-operable control device are ignored by the processor 102. This capability may be useful to prevent a user from inadvertently causing multiple changes in the speed of the moving image to occur faster than the user's neural pathways can be retrained. FIG. 5 illustrates this concept. Arrows 240a, 240b, and 240c indicate time points at which the user activated the user-operable control device 145. Following activation of the user-operable control device 145 at time point 240a, a threshold time period (TH) begins during which any additional activations of the user-operable control device 145 will be ignored. The user has activated the user-operable control device in this example at 240b and because 240b is within the TH time period, the processor 102, programmed with the TH time period, ignores the input control signal from the user-operable control device at that point. However, the next activation of the user-operable control device occurs at 240c, which is outside the TH time period, and the processor will respond to that input control signal to adjust the speed of the moving image.

Figure 6:
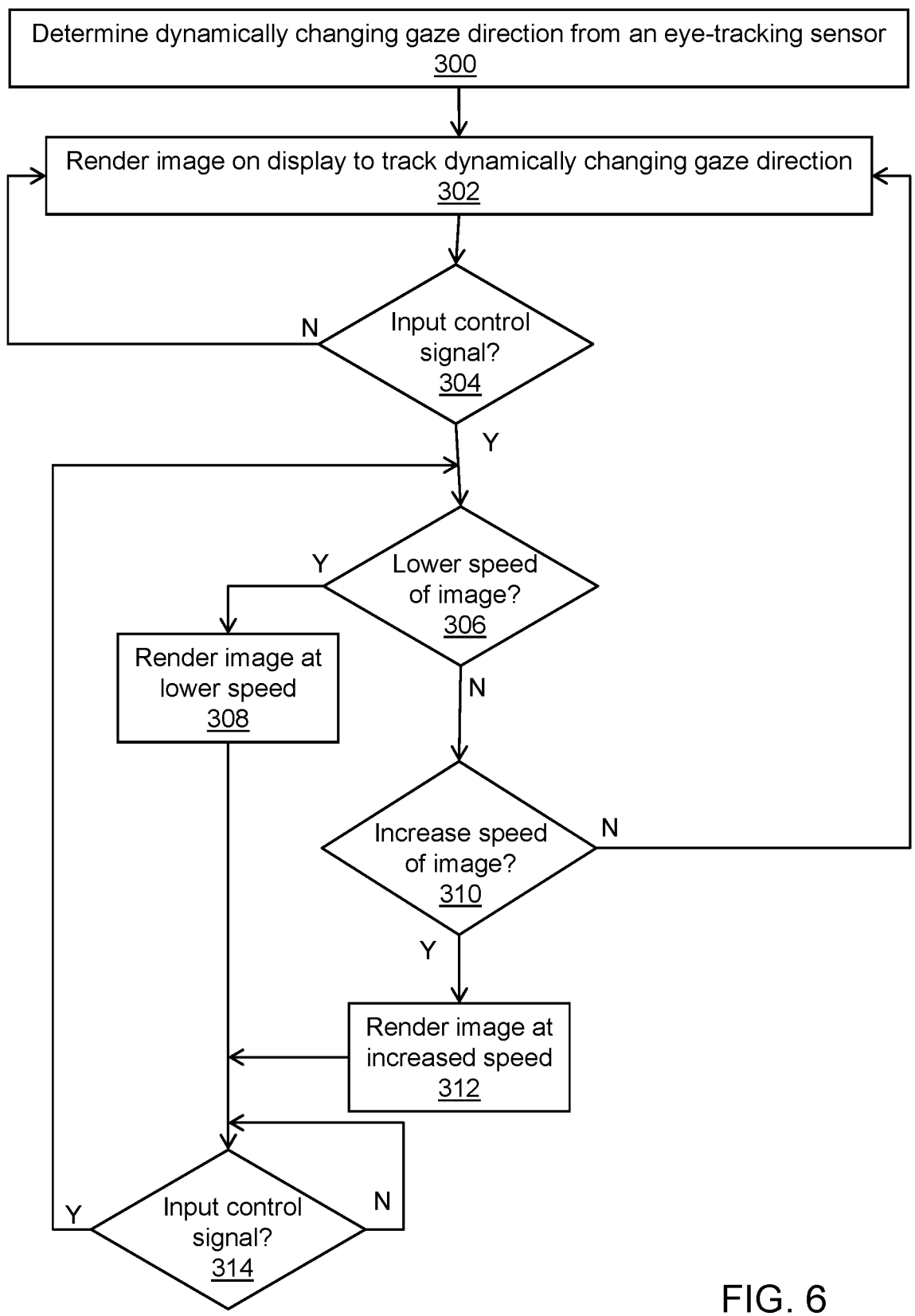
FIG. 6 shows another example of a method.

FIG. 6 shows another method example. The operations may be performed in the order shown, or in a different order. At 300, the method includes determining the dynamically changing gaze direction from an eye-tracking sensor 160. As described above, this operation may be performed by the processor 102 receiving sensor signals from eye-tracking sensor(s) in the headset via the headset interface 130. The signals may be processed by the processor to determine a gaze direction for the user. At 302, the method includes rendering an image (e.g., a geometric shape) on the headset's display(s) to track the dynamically changing gaze direction.

The user then may use the user-operable control device 145 to command the console 100 to perform any of multiple functions (e.g., slow down the image, speed up the image, or revert back to rendering the image to track the eye movements). At 304, the method includes determining whether the console has received an input control signal. This operation may be performed by polling the user-operable control device or through an interrupt mechanism in which an input control signal from the user-operable control device interrupts the processor 102. If no input control signal is detected, then control loops back to 302.

If, however, an input control signal is detected, then at 306 the method includes determining whether the input control signal indicates that the processor 102 is to lower the speed of the rendered moving image. If the input control signal indicates that the moving image speed is to be lowered, then at 308 the processor 102 renders the image at a lower speed (e.g., lowers the speed by predetermined amount or based on a value encoded in the input control signal itself). At this point, the image is not tracking the dynamically changing gaze direction (although presumably over the next few seconds or minutes the user's eye movements will also slow down to track the image) and control passes to 314 to await another input control signal from the user-operable control device 145.

If the input control signal is not determined at 306 to be indicative of a request to lower the moving image speed, then at 310 the method includes determining whether the speed is to be increased. If the speed is to be increased, then the processor at 312 renders the image at the increased speed (either a predetermined amount of speed increase or an amount of speed increase indicated by the input control signal itself). Control then flows to 314 to await another input control signal for further action.

If the input control signal is not to decrease the speed of the image or to increase its speed, then in this example the processor 102 executes operation 302 to again render the image so as to track the dynamically changing gaze direction. In this example, the user has three options to control the speed of the image—increase the speed, decrease the speed, or revert back to the mode in which the moving image is rendered to track the user's eye movements as determined from the eye-tracking sensor signals. If additional user selected functions are possible, then the processor may affirmatively determine that the input control signal comprises a request to render the image tracking to the user's eye movements.

Figure 7:
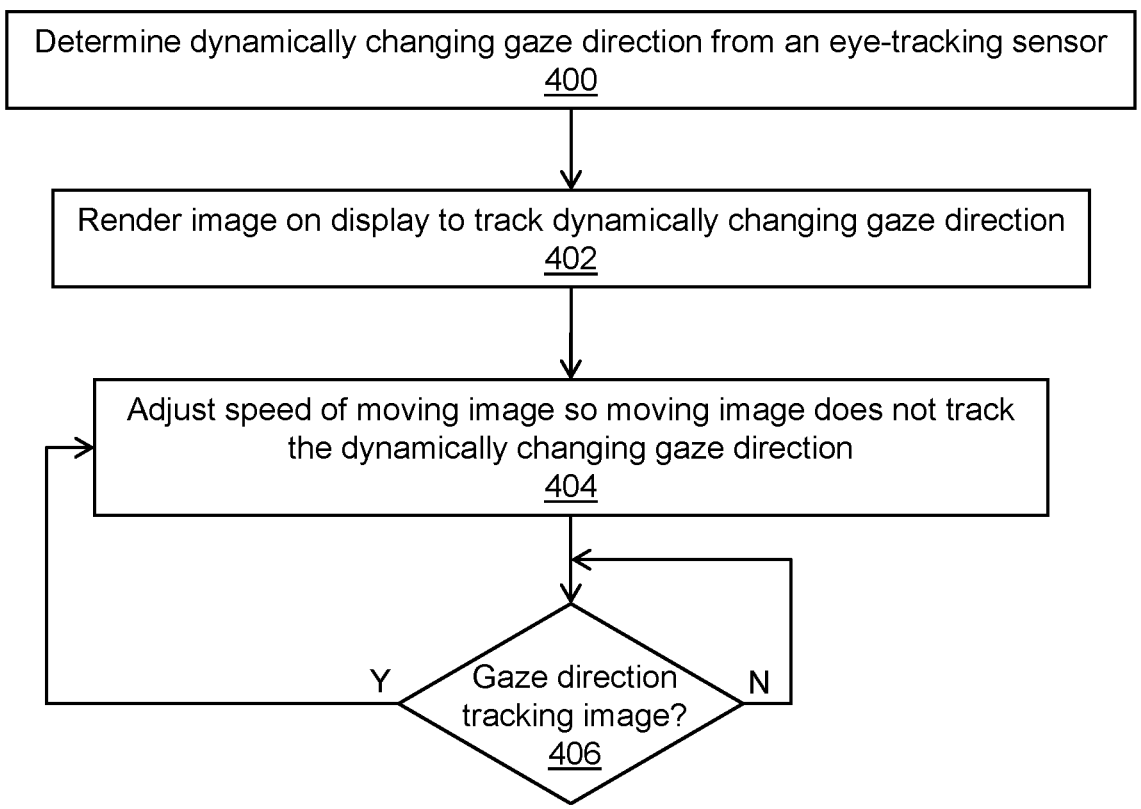
FIG. 7 shows an example of method in which the system automatically adjusts the speed of a moving image based on eye-tracking sensor signals.

FIG. 7 illustrates an example in which the console automatically adjusts the speed of the moving image without the user manually activating the user-operable control device 145. At 400, the method includes determining the dynamically changing gaze direction from an eye-tracking sensor 160. As explained above, this operation may be performed by the processor 102 receiving sensor signals from eye-tracking sensor(s) in the headset via the headset interface 130. The signals may be processed by the processor to determine a gaze direction for the user. The gaze direction may be represented as a location on the display at which the user's eye is determined to be pointing.

At 402, the method includes rendering an image on the headset's display(s) to track the dynamically changing gaze direction. As explained above, the rendered image tracking the changing gaze direction may include rendering the image on the display at the precise location at which the user's eye is pointing, or another location offset from the display location at which the eye is pointing but still moving at generally the same speed and direction as the eye movement and having the same general oscillation frequency.

Once the image is rendered on the display and tracks the user's own eye movements, the image should appear to be stationary to the user with nystagmus. At this point, the processor adjusts the speed of the moving image (404) so that the image no longer tracks the dynamically changing gaze direction of the user. For example, the speed of the image may be reduced. The adjustment may be in predetermined increments as explained above. The change in speed may be gradual enough so as not to be perceptible by the user. The change in speed may be increments or may be continual.

At 406, the processor 102 processes the sensor signals and determines whether the user's gaze direction is tracking the moving image. The processor calculates the locations on the display at which the moving image is to be located. The sensor signals from the eye-tracking sensor 160 can be processed by the processor 102 to determine whether the user's eye(s) is(are) tracking the moving image. When the processor determines that the user's gaze direction is tracking the moving image, then control loops back to 404 and the speed of the moving image is again adjusted (e.g., slowed). This process may repeat with the processor 102 automatically incrementally adjusting (e.g., slowing down) the speed of the moving image as long as the user is able to compensate and slow down his or her own eyes to track the moving image.

If the processor 102 determines that the user's gaze direction is not able to track the moving image (e.g., after a predetermined time period has elapsed), the processor may cause the speed of the moving image to increase to again allow the user's gaze direction to track the moving image. The predetermined time period to allow the speed of the user's gaze direction to automatically change to track the moving speed of the image may be preconfigured (e.g., 30 seconds, 1 minute, etc.) or may be manually controlled by another person monitoring the training session.

The above discussion is meant to be illustrative of the principles and various examples of the present disclosure. Numerous variations and modifications become apparent to those skilled in the art once the above disclosure is fully appreciated. It is intended that the following claims be interpreted to embrace all such variations and modifications.

What is claimed is:

1. A system, comprising:
    a processor;
    storage accessible by the processor and storing executable machine instructions;
    a first interface coupled to the processor, the first interface to provide video data to a first display within a headset and receive eye-tracking sensor signals; and
    a second interface coupled to the processor, the second interface to receive an input control signal from a user-operable control device;
    wherein, when executed, the machine instructions cause the processor to:
        render a moving image on the first display at an oscillation frequency based on the eye-tracking sensor signals; and
        responsive to the input control signal, lower the oscillation frequency of the moving image.

2. The system of claim 1, wherein the machine instructions cause the processor to:
    determine a gaze direction using the eye-tracking sensor signals;

render the moving image based on the determined gaze direction; and calculate the oscillation frequency of the moving image.

3. The system of claim 1, wherein the first interface is to provide the video data to a second display within the headset, one display associated with each eye of two eyes, and to receive eye-tracking sensor signals for each eye, and wherein the machine instructions cause the processor to:

render the moving image on each of the first and second displays commensurate with the eye-tracking sensor signals for the associated eye;

calculate independent oscillation frequencies for the moving images rendered on the first and second displays; and responsive to the input control signal, lower each of the oscillation frequencies.

4. The system of claim 1, wherein the machine instructions cause the processor to lower the oscillation frequency by a predetermined amount.

5. The system of claim 1, wherein the machine instructions cause the processor to lower the oscillation frequency by an amount indicated by the input control signal.

6. The system of claim 1, wherein, responsive to lowering the oscillation frequency, the machine instructions cause the processor to ignore additional input control signals to further lower the oscillation frequency for a threshold period of time.

7. The system of claim 1, wherein, after having lowered the oscillation frequency of the moving image and responsive to receipt of a second control signal by the second interface, the machine instructions cause the processor to:

determine a gaze direction using the eye-tracking sensor signals; and render the moving image based on the determined gaze direction.

8. A system, comprising:

a processor;

storage accessible by the processor and storing executable machine instructions;

a first interface coupled to the processor, the interface to provide video data to a first display within a headset and receive eye-tracking sensor signals; and a second interface coupled to the processor, the second interface to receive an input control signal from a user-operable control device;

wherein, when executed, the machine instructions cause the processor to:

determine a gaze direction using the eye-tracking sensor signals;

render a moving image on the first display to track the gaze direction; and responsive to the input control signal, slow the moving image such that the moving image no longer tracks the determined gaze direction.

9. The system of claim 8, wherein the first interface is to provide the video data to a second display within the headset and to receive eye-tracking sensor signals for each of two eyes, and wherein the machine instructions cause the processor to:

determine a gaze direction of each of the two eyes using the eye-tracking sensor signals for each eye;

render the moving image on each of the first and second displays to track the gaze direction of the respective eye; and responsive to the input control signal, slow the moving image for each of the first and second displays such that the moving image no longer tracks the determined gaze direction.

10. The system of claim 8, wherein the machine instructions cause the processor to slow the moving image by a predetermined amount.

11. The system of claim 8, wherein, responsive to a second input control signal from the user-operable control device, the machine instructions cause the processor to increase a speed of the moving image.

12. The system of claim 8, wherein the machine instructions cause the processor to calculate an oscillation frequency of the moving image on the first display.

13. A non-transitory machine-readable storage medium encoded with instructions executable by a processor, the machine-readable storage medium comprising:

instructions to determine a dynamically changing gaze direction from an eye-tracking sensor signal;

instructions to cause a moving image to be rendered on a display to track the determined dynamically changing gaze direction;

instructions to adjust a speed of the moving image such that the moving image does not track the determined dynamically changing gaze direction;

instructions to determine, based on the eye-tracking sensor signal, whether the dynamically changing gaze direction is tracking the adjusted speed of the moving image; and instructions to, responsive to a determination that the dynamically changing gaze direction is tracking the adjusted speed of the moving image, again adjust the speed of the moving image.

14. The non-transitory machine-readable storage medium of claim 13, wherein the instructions to adjust the speed of the moving image comprise instructions to adjust the speed by a predetermined amount.

15. The non-transitory machine-readable storage medium of claim 13, wherein the moving image comprises a geometric shape on a solid background.

* * * * *